(12) United States Patent
DiFoggio et al.

(10) Patent No.: US 7,826,050 B2
(45) Date of Patent: Nov. 2, 2010

(54) SYSTEM AND METHOD FOR DUAL PATH LENGTH OPTICAL ANALYSIS OF FLUIDS DOWNHOLE

(75) Inventors: Rocco DiFoggio, Houston, TX (US); Paul A. Bergren, Houston, TX (US); Francisco Galvan-Sanchez, Houston, TX (US); Daniel T. Georgi, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 461 days.

(21) Appl. No.: 11/850,434

(22) Filed: Sep. 5, 2007

(65) Prior Publication Data

US 2009/0059332 A1    Mar. 5, 2009

(51) Int. Cl.
*G01N 21/00* (2006.01)
(52) U.S. Cl. .................. 356/241.1; 356/241.5; 356/432
(58) Field of Classification Search ............. 356/241.1, 356/241.3, 241.4, 241.5, 432
See application file for complete search history.

(56) References Cited

U.S. PATENT DOCUMENTS

| | | | | |
|---|---|---|---|---|
| 2,912,895 A | * | 11/1959 | Houston | ............. 356/413 |
| 4,427,634 A | * | 1/1984 | Truglio | ............. 422/99 |
| 4,762,798 A | * | 8/1988 | Deutsch | ............. 436/67 |
| 4,786,171 A | * | 11/1988 | LeFebre et al. | ............. 356/326 |
| 5,044,755 A | | 9/1991 | Landa et al. | |
| 5,303,036 A | | 4/1994 | McLachlan et al. | |
| 5,311,283 A | | 5/1994 | Heeschen | |

FOREIGN PATENT DOCUMENTS

| | | | |
|---|---|---|---|
| JP | 2005-007835 | | 1/2005 |
| JP | 2006194775 A | * | 7/2006 |

* cited by examiner

*Primary Examiner*—Roy Punnoose
(74) *Attorney, Agent, or Firm*—G. Michael Roebuck (57) ABSTRACT

A method is disclosed for changing an optical path length through a fluid downhole, comprising interspersing an optically transmissive member into a first optical path through the fluid, thereby creating a second shorter optical path through the fluid. In another embodiment, the method further comprises measuring an intensity of light, $I_1$ transmitted through the first optical path; measuring an intensity of light, $I_2$ transmitted through the second optical path; and estimating an optical property for the second optical path from the ratio, $I_1/I_2$. A system is disclosed for changing an optical path length through a fluid downhole, comprising a fluid passage between two optically transmissive windows for the fluid downhole, the fluid passage having a first optical path through the fluid; and an optically transmissive member for insertion into the first optical path, thereby creating a second shorter optical path through the fluid.

24 Claims, 8 Drawing Sheets

SYSTEM AND METHOD FOR DUAL PATH LENGTH OPTICAL ANALYSIS OF FLUIDS DOWNHOLE

FIELD OF THE DISCLOSURE

The field of the present invention relates to a dual path length optical cell for windowed formation-fluid sample tanks.

BACKGROUND OF THE DISCLOSURE

In underground drilling applications, such as oil and gas or geothermal drilling, a borehole is drilled through a formation deep into the earth. Such boreholes are drilled or formed by a drill bit connected to the end of a series of sections of drill pipe, so as to form an assembly commonly referred to as a "drill string". The drill string extends from the earth's surface to the bottom of the borehole. As the drill bit rotates, it advances into the earth, thereby forming the borehole. In order to lubricate the drill bit and flush cuttings from the drill bit's path as it advances, a high pressure fluid, referred to as "drilling mud", is directed through an internal passage in the drill string and out through the drill bit. The drilling mud then flows to the surface through an annular passage formed between the exterior of the drill string and the surface or interior wall of the borehole.

The distal or bottom end of the drill string, which includes the drill bit, is referred to as a "downhole assembly". In addition to the drill bit, the downhole assembly often includes specialized modules or tools within the drill string that make up an electrical system for the drill string. Such modules often include sensing modules. In many applications, the sensing modules provide the drill string operator with information regarding the formation as it is being drilled through, using techniques commonly referred to as "measurement while drilling" (MWD) or "logging while drilling" (LWD). For example, resistivity sensors may be used to transmit and receive high frequency signals (e.g., electromagnetic waves) that travel through the formation surrounding the sensor.

As can be readily appreciated, such an electrical system may include many sophisticated electronic components, such as the sensors themselves, which in many cases include printed circuit boards. Additional associated components for storing and processing data in the control module may also be included on printed circuit boards.

SUMMARY OF THE INVENTION

A method is disclosed for changing an optical path length through a fluid downhole, the method comprising interspersing an optically transmissive member into a first optical path through the fluid. Interspersion of the member creates a second shorter optical path through the fluid. In another embodiment, the method further comprises measuring an intensity of light, $I_1$ transmitted through the first optical path; measuring an intensity of light, $I_2$ transmitted through the second optical path; and estimating an optical property for the second optical path from the ratio, $I_1/I_2$.

A system is disclosed for changing an optical path length through a fluid downhole, the system comprising a fluid passage between two optically transmissive windows for the fluid downhole, the fluid passage having a first optical path through the fluid; and an optically transmissive member for insertion into the first optical path, thereby creating a second shorter optical path through the fluid.

DETAILED DESCRIPTION OF ILLUSTRATIVE EMBODIMENTS

In a particular illustrative embodiment, a method is disclosed for changing an optical path length through a fluid downhole, the method comprising interspersing an optically transmissive member into a first optical path through the fluid, thereby creating a second shorter optical path through the fluid. In another particular embodiment, the method further comprises measuring an intensity of light, $I_1$ transmitted through the first optical path; measuring an intensity of light, $I_2$ transmitted through the second optical path; and estimating an optical property for the second optical path from the ratio, $I_1/I_2$. In another particular embodiment, the method further comprises estimating a fluid property from the optical property.

In another particular embodiment, the method further comprises interspersing a second optically transmissive member into the first optical path, thereby creating a third optical path shorter than the second optical path; measuring an intensity of light, $I_2$ transmitted through the fluid along the second optical path; measuring an intensity of light, $I_3$ transmitted through the fluid along the third optical path; and estimating an optical property for the fluid through the third path from the ratio, $I_2/I_3$. In another particular embodiment, the method further comprises measuring an intensity of light, $I_1$ transmitted through the fluid along the first optical path; If $I_1$ is below a predetermined value, interspersing a second optically transmissive member into the first optical path, thereby creating a third optical path shorter than the second optical path; measuring an intensity of light, $I_2$ transmitted through the fluid along the second optical path; measuring an intensity of light, $I_3$ transmitted through the fluid along the third optical path; and estimating an optical property for the fluid through the third path from the ratio, $I_2/I_3$.

In another particular embodiment of the method the optically transmissive member further comprises a plurality of sections, each section having a different thickness, the interspersing further comprising interspersing at least two of the plurality of sections into the first optical path to create different optical path lengths through the fluid. In another particular embodiment of the method the optically transmissive member is round, having radial steps of varying thickness. In another particular embodiment of the method, the optically transmissive member has steps of varying thickness along a longitudinal axis. In another particular embodiment of the method, the fluid is a substantially a gas. In another particular embodiment of the method the first optical path traverses a fluid between two optically transmissive windows, the method further comprising applying a force to the optically transmissive member to press the optically transmissive member against a surface of an adjacent one of the two optically transmissive windows, thereby substantially thinning any remaining layer of fluid between them and reducing reflections of light from an interface between the optically transmissive member and the window surface whenever both have substantially the same refractive index but the thin layer of fluid between them has a different refractive index.

In another particular embodiment of the method a distance between the optically transmissive member and the adjacent optically transmissive window is less a few wavelengths of light passing through the optical path. In another particular embodiment of the method the optically transmissive windows and the optically transmissive member have a substantially similar index of refraction to minimize reflection at the interface, when they are in contact. In another particular embodiment of the method the optically transmissive windows and the optically transmissive member are made of sapphire.

In another particular embodiment a system is disclosed for changing an optical path length through a fluid downhole, the system comprising a fluid passage between two optically transmissive windows for the fluid downhole, the fluid passage having a first optical path through the fluid; and an optically transmissive member for insertion into the first optical path, thereby creating a second shorter optical path through the fluid.

In another particular embodiment of the system, the system further comprises a positioner attached to the optically transmissive member that moves the optically transmissive member into the first optical path creating the second optical path. In another particular embodiment of the system the optically transmissive member further comprises a plurality of sections, each section having a different thickness, thereby creating a different path length through the fluid when each section is inserted into the first optical path. In another particular embodiment of the system, the system further comprises a force member in contact the optically transmissive member, wherein the force member presses the optically transmissive member toward an adjacent optically transmissive window, thereby reducing reflection of light from an interface between the optically flat transmissive member and the adjacent optically flat transmissive window.

In another particular embodiment of the system, the adjacent optically transmissive window forms a wall of the fluid passage. In another particular embodiment of the system, the system further comprises a light sensor for measuring light passing through the fluid along the first optical path and the second optical path. In another particular embodiment of the system, the system further comprises a light source positioned adjacent an optically transmissive window; a filter positioned between the light source and a light sensor, the filter selectively passing frequencies of light from the light source to the light sensor along the first and second optical paths through the fluid; and a processor for estimating an optical property of the fluid from the light measured passing through the fluid along the first path and the second path.

In another particular embodiment of the system, the optically transmissive member and the optically transmissive windows have substantially the same index of refraction. In another particular embodiment of the system, the optically transmissive member and the optically transmissive windows are made of sapphire. In another particular embodiment of the system, the fluid is a gas. In another particular embodiment of the system, the system further comprises a shape for the optically transmissive member selected from the group consisting of round having radial steps of varying thickness and substantially rectangular having steps of varying thickness along a longitudinal axis.

In another particular embodiment, a downhole tool is disclosed for estimating a property of a fluid, the downhole tool comprising a tool housing suitable for traversing a borehole in an earth borne fluid formation; a port in the tool housing for entry of fluid from the formation; a fluid passage in fluid communication with the port, the fluid passage having a first optical path through the fluid; an optically transmissive member movably mounted for insertion into the first optical path length, thereby creating a second shorter optical path through the fluid; a positioner attached to the optically transmissive member that inserts the optically transmissive member into the optical path; a light sensor for measuring light passing through the fluid along the first path and the second path; a filter positioned between the light sensor and the light source for selectively passing frequencies of the light from the light source to the light sensor along the first and second optical path; and a processor for estimating an optical property of the fluid from the light measured passing through the fluid along the first path and along the second path.

In many prior downhole fluid optical analysis systems, the first step in estimating a downhole fluid's absorption spectra has been to determine how much light at each wavelength would have gone through the sample cell had the cell been empty. This amount of light passing through the sample-filled cell divided by the amount of light that would have passed through the empty cell is used to calculate the transmittance of the sample if no correction is made for the loss of light due to reflection at the window-air interface, which is generally more reflective than the window-fluid interface. The base-ten logarithm of the inverse of the transmittance is the absorbance which is also called the optical density (OD) and which is a measure of the darkness of a fluid, The OD can be measured and plotted versus wavelength for determining a property of a fluid. This step had been performed uphole at the surface for an empty cell and the readings stored for use later to calculate absorbance spectra gathered downhole. The next step in estimating absorbance was to divide that amount of light traversing an empty cell by an amount of light traversing the cell when it is full of fluid and take the base ten logarithm of that ratio.

The empty-cell measurement has been performed by collecting the transmission spectra of light traversing an empty cell and then storing this empty-cell spectrum for later use. However, because of changes caused by spectrometer aging or by the exact positioning and fixturing of the input or output optical fibers to the cell, it is desirable to obtain the empty-cell spectrum within no more than a few minutes of obtaining the—filled-cell spectrum. For performing qualitative spectroscopy (fluid type identification), such high accuracy may not matter, but to reliably perform quantitative spectroscopy and estimate fluid properties from these spectra (that is, for example, to use chemometrics to estimate a property of a fluid from the optical spectra measured down hole), it is desirable to reduce as many spurious effects as possible. Solid fixturing and a dual path length can be useful to obtain reproducible quantitative measurements.

In another particular illustrative embodiment, using a dual path length cell, optical transmission spectra are collected for each of at least two different path lengths. The first and longer path length is the distance between a pair of pressure-holding sapphire windows, which form a fluid passage way or cell. The first optical path length through the fluid is formed when there is no optically transmissive member, such as an insertable sapphire plate positioned between these windows. The second and subsequent, shorter fluid path lengths occur when a sapphire plate or plates are positioned between the two pressure-holding sapphire windows. The sapphire plate occupies a portion of the path length through the fluid that was previously occupied by the fluid. Thus, when the sapphire plate is inserted into the path length, less fluid occupies the cell and light traverses a shorter distance across the fluid in the cell. There are less losses (absorbance) associated with a shorter path through the fluid. In another illustrative embodiment, the reference spectrum for the shorter path length of fluid is used as the reference spectrum for the absorbance and optical density calculations, instead of using a previously recorded spectrum of an empty, air-filled cell as a reference. The insertion of the sapphire member, an optically transmissive member enables the fluid passage or fluid cell to be self referencing for OD measurements. Thus, comparative measurements for different path lengths through the fluid can be made under essentially identical environmental conditions and at essentially close to the same time or close enough to the same time so that variations in environmental conditions are substantially minimized.

The optical absorbance or optical density (OD) associated with a fluid path length can be estimated as the base ten logarithm of the ratio of amount of light, I1, transmitted through the short path length through the fluid to the amount of light, I2, transmitted through the long path length through the fluid. Note that the path length difference between the long and short path lengths is the thickness of the sapphire plate, which stays substantially constant even under high pressure because sapphire is extremely stiff in compression compared to metals. Thus, in another particular illustrative embodiment, the dual path length configuration substantially compensates for increased separation (path length) between the pressure-holding windows that can occur as the fluid pressure increases and the metal framework holding the windows is slightly elastically stretched.

The dual path length configuration also substantially compensates for any dirt or haze on the outside surfaces of the windows because both short and long path length spectra measurements include this contamination so the effects are removed upon taking the spectral ratio to compute absorbance. The dual path length configuration also substantially avoids variability in the positioning of optical fibers that might occur if collecting the spectrum of a fluid-filled cell and then using the spectrum of another cell that is empty. It has been observed that at high pressures downhole (such as 30 thousand pounds per square inch (KPSI)), a 2 mm path length between a pair of rigidly mounted sapphire windows may stretch by as much as 5 percent as the mounting metal that is holding the sapphire windows is slightly distorted under pressure downhole.

In another embodiment, the dual path length of an illustrative embodiment is based on a sapphire insert that substantially eliminates this distortion under pressure effect because the short and long path length spectra both include this increased path length so its effect is removed upon taking the spectral ratio to compute absorbance. The dual path length provided in an illustrative embodiment substantially eliminates the reflection differences between a fluid sample and reference spectra for an empty cell, which are caused by differences between fluid and window refractive indices. The reflection caused by refractive index mismatch is greatest when air is in the empty sample cell. This is because air's refractive index is substantially different from that of sapphire. In another embodiment, because the optical fixture is not changed between downhole sampling and reference scans, the dual path length of an illustrative embodiment also substantially avoids the effects of inconsistencies in fixture geometry between taking an empty cell reference spectrum and a full cell absorption spectrum as, for example, when using a fiber optic multiplexer to alternate between reading light entering the cell and light exiting the cell. In another illustrative embodiment, the pressure-holding windows could be moved towards or away from one another by a known distance to obtain the fluid spectra at two different path lengths, although doing so downhole would require considerable energy (force times the distance moved). The dual path length approach, which uses a moveable insert that is entirely immersed in the high pressure fluid, eliminates the need to expend such energy although it is still an alternative.

Another particular embodiment shines broad band or collimated filtered light through a pair of sapphire windows to collect optical absorption spectra of live formation fluid that is between these two windows while the sample cell is still down hole in the field. In another illustrative embodiment, based on correlations to visible and near infrared optical spectra, the system and method estimate the fluid's gas-oil ratio (GOR) and other fluid property parameters such as API gravity and percentages of asphaltenes, aromatics, and saturates. In another embodiment, the two path lengths enable the fluid cell or fluid passage to be self-referencing. Thus, there is no need to obtain a reference spectrum through an empty cell. Another illustrative embodiment provides a dual path length cell by providing a moveable thin sapphire plate that can be positioned between two fixed, pressure-holding sapphire windows. This positioning is performed by using a screw mechanism, or by using gravity when the tank is tilted, or by using a magnet or by an electromagnetic or electronic moveable positioner. In another particular embodiment, the positioner moves a longitudinal sapphire plate along a longitudinal axis for the sapphire plate, having sections of variable thickness along the longitudinal axis. In another particular embodiment, the positioner angularly positions or rotates a round sapphire plate around a center axis for the round sapphire plate, the round sapphire plate having sections of variable thickness over different angular regions.

Another embodiment provides a positioner to move the pressure-holding windows towards or away from one another by a known distance. For some embodiments (gravity or magnetic actuation), such as the insertable sapphire plate, there would be no change in fluid pressure or volume as the insert was moved into or out of position between the sapphire pressure-holding windows. High pressure downhole fluid passes between these windows. On the opposite sides of these windows, the pressure is close to atmospheric pressure.

In another particular embodiment, a 2-mm path length spectra of heavy oils often exceeds the 3 to 3.5 OD (Optical Density) dynamic range of another illustrative embodiment. For a shorter, 1-mm path length, each point of each spectrum would have half of the 2-mm OD value, thus keeping the heavy oil spectra within the dynamic range of another illustrative embodiment. Thus, it would be advantageous to shorten the 2 mm path length to 1 mm to reduce the OD values so that they are within the dynamic range of the system.

In another embodiment, for heavy oils (such as 10 API gravity), a path length of 2 mm is too long for the spectral absorbance to stay within a dynamic range (about 3 to 3.5). In one particular example, it is not possible to the spectral signature of 7% water contamination mixed into a 10 API heavy oil sample due to dynamic range limitations. The reason was that the OD spectrum of the mixture exceeded the dynamic range of the tool. By cutting the standard 2-mm path length in half to only 1 mm, using the optically transmissive insert, cuts in half the absorbance at each channel and thus stays within the dynamic range. An added advantage of a dual path length cell, whose path length can be changed downhole while running, is that an illustrative embodiment can collect a downhole reference spectrum (a "calibration" spectrum) at the downhole temperature and for a fluid having the same refractive index as the final sample instead of relying on memorized values for a reference spectrum created in the lab in an air-filled cell. An optical insert, consisting of a flat sapphire plate, is moved back and forth into and out an optical path of the 2-mm gap between the existing round sapphire windows.

In another particular embodiment, the insert has magnetic end pieces, which allow the sapphire plate to be positioned or moved back and forth using electromagnets, and so can change the path length of fluid through which the light passes by displacing some of the fluid in the path with the sapphire insert. Note that, in this design, insertion or removal of the flat sapphire plate is not performed against any pressure differential and does not require a sliding seal that has a high pressure differential across it. Appropriate mechanical stops are placed on each side to insure that the insert is pulled all the way to one side or the other under the influence of the corresponding electromagnet or another positioner. If the thickness of the sapphire plate is 1 mm, then the effective fluid path length when this place is moved into the 2 mm gap between the existing round sapphire windows equals 2 mm−1 mm=1 mm.

Furthermore, if the fluid composition is not changing, then the base ten logarithm of the ratio of the 1-mm transmission spectrum to the 2-mm transmission spectrum equals the 1-mm absorbance spectrum. Using one path length of fluid as the reference spectrum for another path length substantially eliminates questions and uncertainty around the memorized calibration constants of the empty cell being out of date. The dual path length also substantially reduces the small absorbance error associated with not correcting for the variation in the amount of reflection at the window-fluid interface, which varies depending on whether the fluid is air (refractive index of approximately 1.0), water (RI typically 1.33-1.38) or oil (RI typically 1.40-1.55). The window-fluid reflection depends on the square of the ratio of the refractive index of the window to the refractive index of the fluid.

Laboratory reference spectrum obtained with air filling the cell indicates that each sapphire-air interface has about 7.5% reflection. This means that only 92.5% of light headed towards the gap between the windows but still traveling inside of the first window ever enters the air in that gap between the windows and only 92.5% of that light which entered the air gap is passed on into the second window. A sapphire-oil interface has much less reflection (about 0.5% to 1.0% reflection) because sapphire and oil have similar reflectivity indices. In general, if the path length between the windows is "D" and the thickness of the transparent insert is "d", and the fraction of light transmitted through fluid of long path length "D" is $f_D$ and the fraction of light transmitted through fluid of short path length "D-d" is $f_{D-d}$ (when the insert displaces a thickness "d" of the fluid), then the absorbance, $A_d$, for a path length equal to the thickness, "d", of the insert is given by, $A_d=\log 10(f_{D-d}/f_D)$.

In another illustrative embodiment, an apparatus is provided in which visible, fluorescent, mid infrared and near infrared (IR) analysis of the fluids is performed. In another embodiment the analysis is performed in the borehole, without having to transport recovered samples of the fluid to the surface for chemical analysis. The infrared portion part of the electromagnetic spectrum of a substance contains absorption features due to the molecular vibrations of the constituent molecules. The absorptions arise from both fundamentals and combination bands and overtones (multiple quanta transitions occurring in the mid- and the near-infrared region from 0.8-2.5 microns). The position (frequency or wavelength) of these absorptions contain information as to the types of molecular structures that are present in the material, and the intensity of the absorptions contains information about the amounts of the molecular types that are present. To use the information in the spectra for the purpose of identifying and quantifying either components or properties a calibration is performed to establish the relationship between the absorbance and the component or property that is to be estimated.

For complex mixtures, where considerable overlap between the absorptions of individual constituents occurs, such calibrations can be accomplished using various chemometric data analysis methods. In complex mixtures, each constituent generally gives rise to multiple absorption features corresponding to different vibrational motions. The intensities of these absorptions will all vary together in a linear fashion as the concentration of the constituent varies. Such features are said to have intensities which are correlated in the frequency (or wavelength) domain. This correlation allows these absorptions to be mathematically distinguished from random spectral measurement noise which shows no such correlation. The linear algebra computations which separate the correlated absorbance signals from the spectral noise form the basis for techniques such as Principal Components Regression (PCR) and Partial Least Squares (PLS). As is well known, PCR is essentially the analytical mathematical procedure of Principal Components Analysis (PCA), followed by regression analysis. PCR and PLS are used to estimate elemental and chemical compositions and to a lesser extent physical or thermodynamic properties of solids, liquids and gases based on their mid- or near-infrared spectra.

These chemometric methods include but are not limited to the collection of mid- or near-infrared spectra of a set of representative samples; mathematical treatment of the spectral data to extract the Principal Components or latent variables (e.g. the correlated absorbance signals described above); and regression of these spectral variables against composition and/or property data to build a multivariate model. The analysis of new samples then involves the collection of their spectra, the decomposition of the spectra in terms of the spectral variables, and the application of the regression equation to calculate the composition/properties.

In another embodiment fluorescent, visible and near and mid IR region light is passed through the fluid sample. A spectrometer measures the spectrum of the transmitted and the back scattered light, and knowing the spectrum of the incident light, transmission and backscattered absorption spectra for the sample are determined. Using absorption spectra of water, gas, crude and refined oils, and drilling fluids, a least squares analysis is performed that models the observed spectra as a weighted sum of the spectra of its components, the least squares analysis giving the composition of the fluid in terms of weights of the various components.

Figure 1:
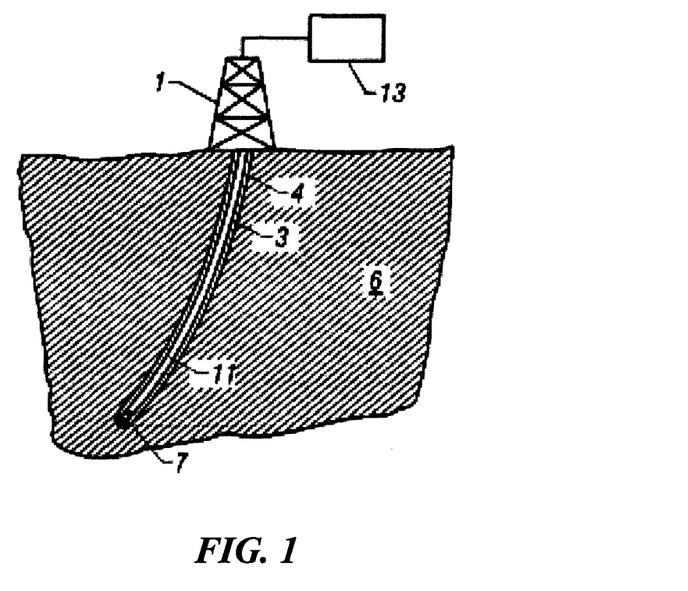
FIG. 1 is a schematic depiction of a particular illustrative embodiment in a monitoring while drilling environment.

Turning now to FIG. 1, in a drilling operation according one particular illustrative embodiment is shown in FIG. 1. A drilling rig 1 drives a drill string 3 that typically is comprised of a number of interconnecting sections. A downhole assembly 11 is formed at the distal end of the drill string 3. The downhole assembly 11 includes a drill bit 7 that advances to form a bore 4 in the surrounding formation 6. A portion of the downhole assembly 11, incorporating an electrical or electronic system 8 according to a particular illustrative embodiment is shown in FIG. 2.

Figure 2:
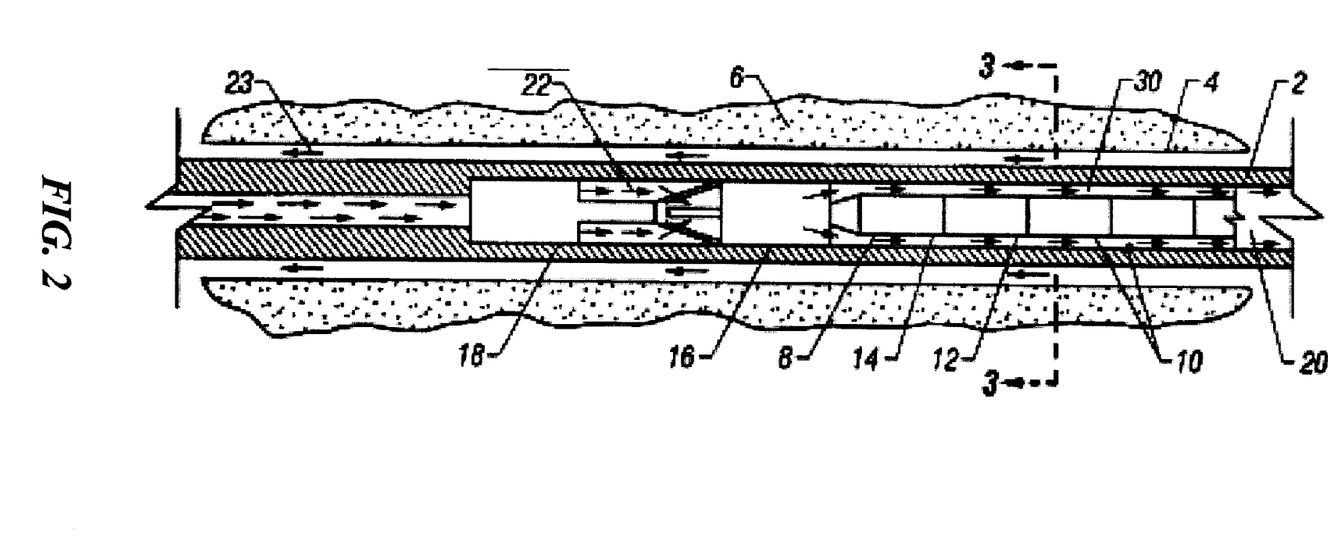
FIG. 2 is a longitudinal cross section through a portion of a down tool attached to the drill string as shown in FIG. 1 incorporating an optical sensor.

Turning now to FIG. 2, the electrical system 8 may, for example, provide information and data to a data acquisition and analysis system 13 located at the surface. In another embodiment, the data acquisition and/or analysis system are located downhole inside the downhole assembly. The electrical system 8 can include but is not limited to one or more electronic components. Such electronic components include those that incorporate transistors, integrated circuits, resistors, capacitors, and inductors, as well as electronic components such as processors, computer readable media containing computer program instructions, electronic filters, spectrometers, including accelerometers, sensing elements including photo detectors, photo sensors, filters, magnetometers, photomultiplier tubes, and strain gages.

The downhole portion 11 of the drill string 3 includes a drill pipe, or collar, 2 that extends through the bore 4. As is conventional, a centrally disposed passage 20 is formed within the drill pipe 2 and allows drilling mud 22 to be pumped from the surface down to the drill bit. After exiting the drill bit, the drilling mud 23 flows up through an annular passage formed between the outer surface of the drill pipe 2 and the internal diameter of the bore 4 for return to the surface. Thus, the drilling mud flows over both the inside and outside surfaces of the drill pipe. Depending on the drilling operation, the pressure of the drilling mud 22 flowing through the drill pipe internal passage 20 will typically be between 1,000 and 20,000 pounds per square inch, and, during drilling, its flow rate and velocity will typically be in the 100 to 1500 GPM range and 5 to 150 feet per second range, respectively.

As also shown in FIG. 2, the electrical system 8 is disposed within the drill pipe central passage 20. The electrical system 8 includes a number of sensor modules 10, a control module 12, a power regulator module 14, an acoustic pulser module 18, and a turbine alternator 16 that are supported within the passage 20, for example, by struts extending between the modules and the drill pipe 2. According to another illustrative embodiment, power for the electrical system 8, including the electronic components and sensors, discussed below, is supplied by a battery, a wireline or any other typical power supply method such as the turbine alternator 16, shown in FIG. 2, which is driven by the drilling mud 22. The sensors are in fluid communication with the drilling mud 22. The turbine alternator 16 may be of the axial, radial or mixed flow type. Alternatively, the alternator 16 could be driven by a positive displacement motor driven by the drilling mud 22, such as a Moineau-type motor. In other embodiments, power could be supplied by any power supply apparatus including an energy storage device located downhole, such as a battery.

Figure 3:
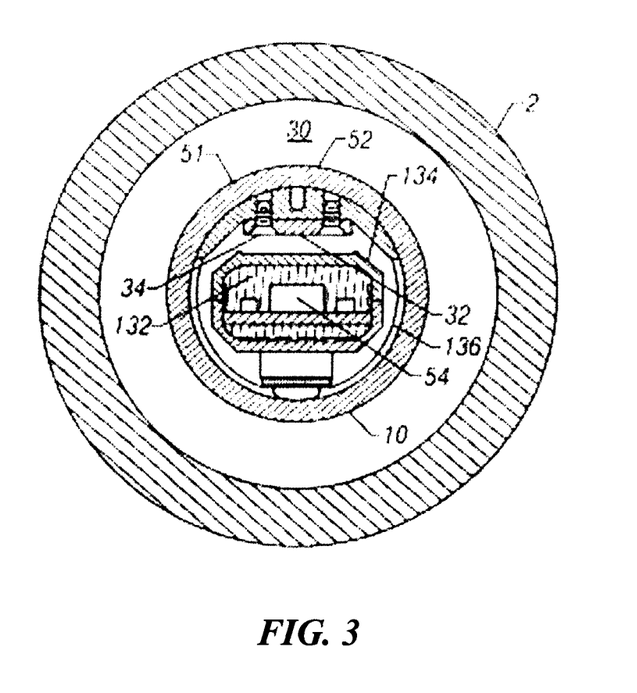
FIG. 3 is a transverse cross section through one of the sensor modules shown in FIG. 2 taken along line III-III.

As shown in FIG. 3, in another embodiment, each sensor module 10 is comprised of a cylindrical housing 52, which in an illustrative embodiment is formed from stainless steel or a beryllium copper alloy. An annular passage 30 is formed between the outer surface 51 of the cylindrical housing 52 and the inner surface of the drill pipe 2. The drilling mud 22 flows through the annular passage 30 on its way to the drill bit 7, as previously discussed. The housing 52 contains an electronic component 54 for the sensor module. The electronic component 54 may, but according to a particular illustrative embodiment, does not necessarily, include one or more printed circuit boards including a processor associated with the sensing device, as previously discussed. Alternatively, the assembly shown in FIG. 3 comprises the control module 12, power regulator module 14, or pulser module 18, in which case the electronic component 54 may be different than those used in the sensor modules 10, although it may, but does not necessarily, include one or more printed circuit boards. According to a particular illustrative embodiment, one or more of the electronic components or sensors in the electrical system 8 are cooled by evaporation of liquid from the liquid supply 132 adjacent to or surrounding electronics 54.

Figure 4:
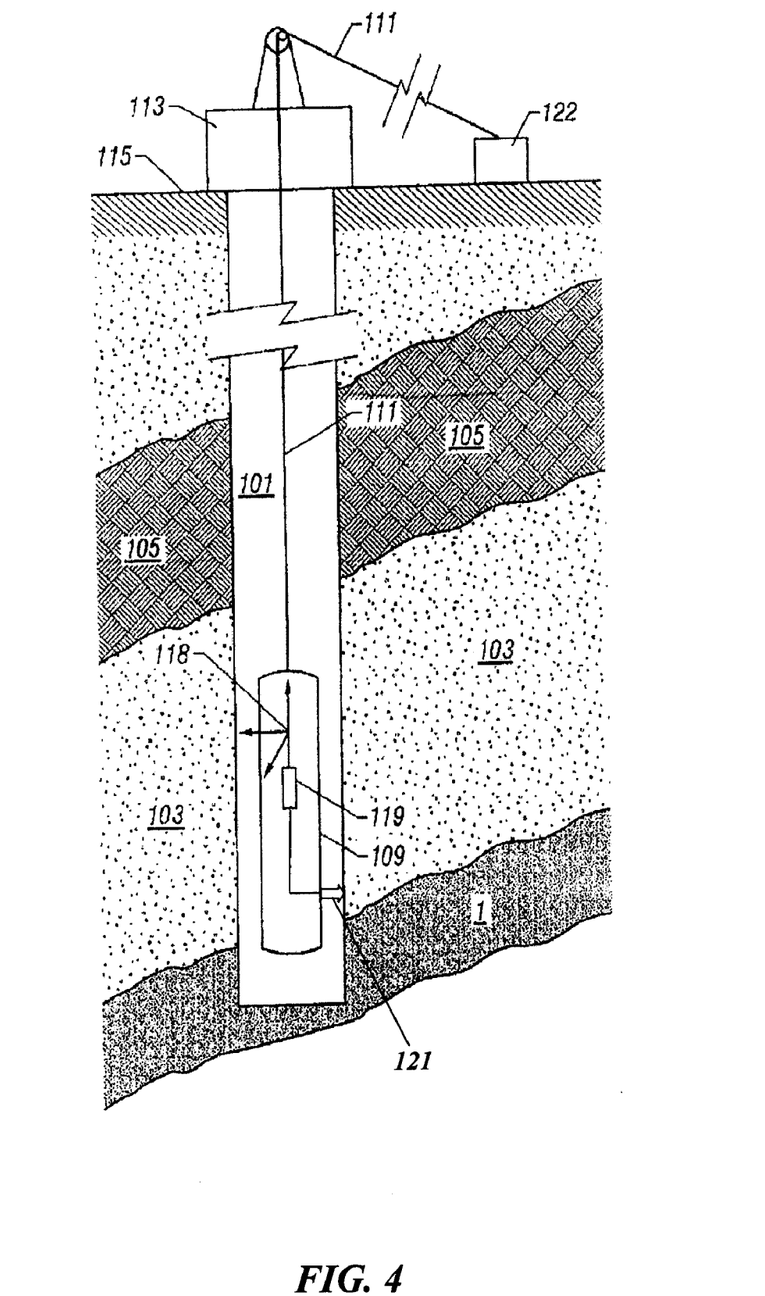
FIG. 4 is a schematic depiction of an illustrative embodiment shown deployed in a wire line environment.

Turning now to FIG. 4 a wire line deployment of the present invention is depicted. FIG. 4 schematically depicts a well bore 101 extending into a laminated earth formation, into which well bore a logging tool including sensors and electronics as used according to the present invention has been lowered. The well bore in FIG. 4 extends into an earth formation which includes a hydrocarbon-bearing sand layer 103 located between an upper shale layer 105 and a higher conductivity than the hydrocarbon bearing sand layer 103. An electronic logging tool 109 having sensors and electronics and a sorption or thermal conductive cooling system, has been lowered into the well bore 101 via a wire line 111 extending through a blowout preventer 113 (shown schematically) located at the earth surface 115. The surface equipment 122 includes an electric power supply to provide electric power to the set of coils 118 and a signal processor to receive and process electric signals from the sensors and electronics 119. Alternatively, a power supply and signal processor are located in the logging tool. In the case of the wire line deployment, the wire line may be utilized for provision of power and data transmission. The electronic logging tool further includes a port or orifice 121 in fluid communication with the fluid or gas in the formation and the sensors. The wire line tool further includes but is not limited to a processor, memory and a database for data acquisition and storage.

Figure 5:
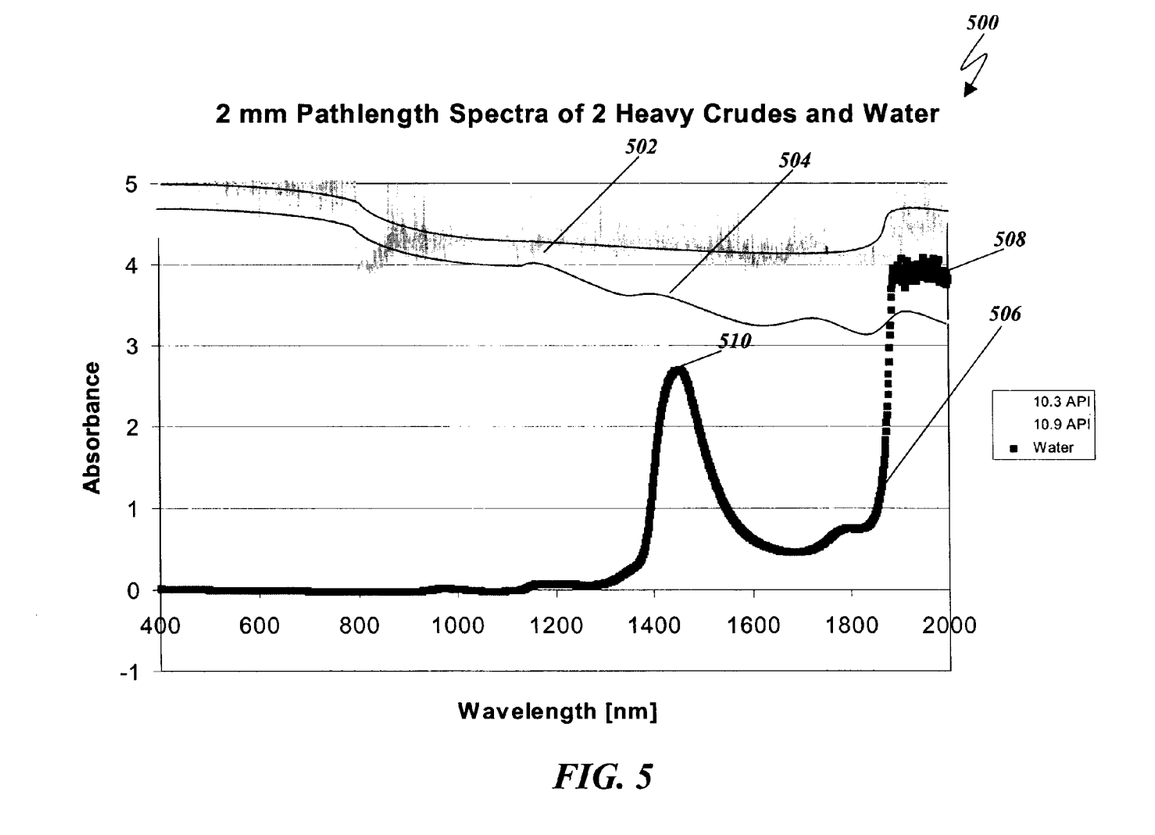
FIG. 5 is a plot of absorbance or optical density (OD) versus wavelength in nanometers for two heavy crude oils and water.

Turning now to FIG. 5 in the illustrated embodiment absorbance or optical density (OD) versus wavelength graph 500 illustrates OD spectra from 0-5 OD for a two 2 mm path length spectra of two heavy crude oils and water. A plot of the optical spectra for water 506 has a peak at approximately 1450 nm 510 and a peak at approximately 1930 nm 508. Note that the water peak at 1930 nm appears at four OD, which is beyond the dynamic range of the tool sensors in an illustrative embodiment. Note also that the heavy crude oils are beyond 4 OD, the upper limit of the dynamic range in the present example where the readings become highly unreliable and non-linear. These out-of-range peaks at 1930 nm and for the heavy crude oils can be lowered and brought into the dynamic range of the tool by shortening the path length through the heavy crude or water. The path length is shortened by inserting the optically transmissive member into the 2 mm path length making the path length through the fluid shorter and allowing more light to pass through, thereby lowering the absorbance or optical density measured for the heavy crude oils and water in these wavelength regions of the optical spectra. The OD is proportional to path length within the dynamic range of the tool. Thus, when the path length is cut in half, for example from 2 mm to 1 mm, a 4 OD measurement for 2 mm should become a 2 OD measurement for 1 mm. An appropriate path length can be estimated by starting with the shortest path length and successively doubling the path length and determining when the linear relationship between path length and OD measurement breaks down. In another particular embodiment, the appropriate long path length is the longest path length at which the linear relationship between OD and path length still exists before breaking down.

Figure 6:
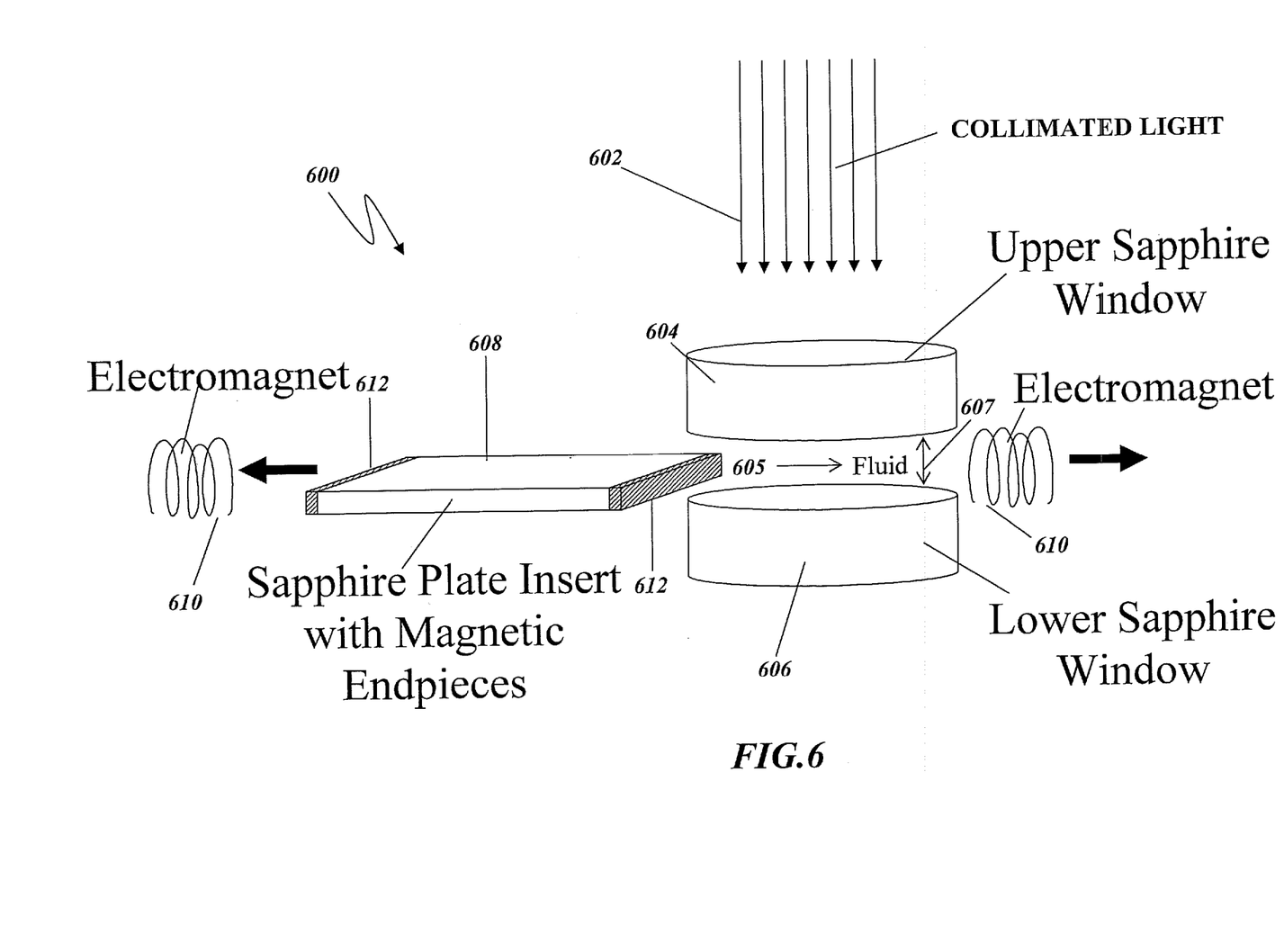
FIG. 6 is a schematic representation of another illustrative embodiment showing a sapphire plate inserted between an upper and lower sapphire window forming a fluid passage or cell.

Turning out to FIG. 6, in another illustrative embodiment a system 600 is provided that provides an optically transmissive member 608 (such as a sapphire window or in another embodiment, some other optically transmissive material) positioned between two optically transmissive members windows 604 and 606. A light beam 602 passes through each optically transmissive window and through the fluid 605 which flows through fluid passage 607. A distance between the interior or adjacent surfaces of optically transmissive windows 604, 606 forms a fluid passage 607 or fluid cell having a path length through the fluid equal to the distance between the adjacent surfaces of windows 604, 606. When the optically transmissive member 608 is inserted into the optical path length through the fluid passage the thickness of the fluid in the fluid passage along the optical path length is reduced by the thickness of the sapphire plate or optically transmissive member 608. For example, the path length between the two optically transmissive windows is 3 mm and the optically transmissive member or sapphire plate has a thickness of 1 mm. The optical path length through the fluid before the optically transmissive member is inserted is 3 mm. The optical path length through the fluid is reduced to 2 mm after the optically transmissive member is inserted into the 3 mm fluid passage.

Figure 7:
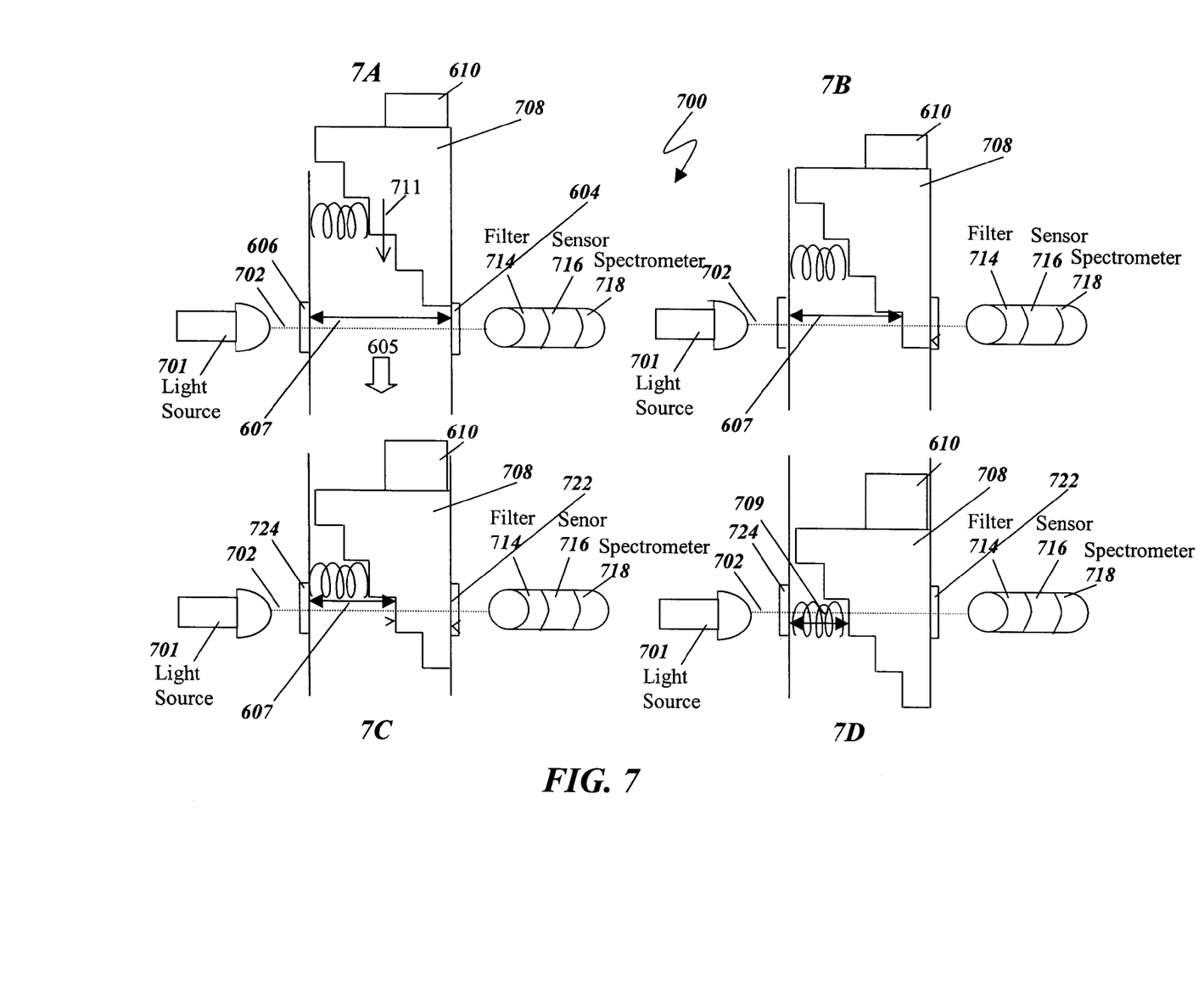
FIG. 7 is a schematic representation of another illustrative embodiment wherein a optically transmissive member having multiple sections of varying thickness is inserted into the in optical path.

Turning now to FIG. 7, optically transmissive member 708 is shown in fluid passage 607 formed by the adjacent surfaces of optically transmissive windows 724 and 722. The optically transmissive member 608 is subjected to the same pressure as fluid 605 in fluid passage 607. Positioner 610 moves the optically transmissive member, along the fluid passage adjacent optically transmissive windows 604, 606.

Turning now to FIGS. 7A-7D, movement of a longitudinally varying thickness optically transmissive member is shown. In the embodiment shown in FIG. 7A-7D, the positioner moves the optically transmissive member in a direction parallel to a longitudinal axis for the member. The optically transmissive member provides a series of varying thickness steps along the longitudinal axis 711 of the member. Thus, as each section of the member is moved into the optical path of the light beam, the optical path through the fluid is shorted by the thickness of the step in the optical member intersecting the light beam. As shown in FIG. 7A, the optically transmissive member positioner has positioned the optically transmissive member so that the member does not intersect light beam 702 shone through the fluid 705 from light source 701. Thus in FIG. 7A the path length is equal to the distance between the two optically transmissive windows.

As shown in FIG. 7B, the optically transmissive member is moved by positioner 610 so that the first and smallest thickness section of optically transmissive member intersects light beam 602 passing through the fluid 605. Thus the path length of a light beam passing through the fluid is now equal to the distance between the two optically transmissive windows minus the thickness of the first section of the optically transmissive member 608 which intersects the light beam 602 passing through the fluid 605. As shown in FIG. 7C, the optically transmissive member is moved by positioner 610 so that the second section of optically transmissive member intersects light beam 602 passing through the fluid 605. Thus the path length of a light beam passing through the fluid is now equal to the distance between the two optically transmissive windows minus the thickness of the second section of the optically transmissive member 608 which intersects the light beam six and two passing through the fluid 605. As shown in FIG. 7D, the optically transmissive member is moved by positioner 610 so that the third section of optically transmissive member intersects light beam 602 passing through the fluid 605. Thus the path length of a light beam passing through the fluid is now equal to the distance between the two optically transmissive windows minus the thickness of the third section of the optically transmissive member 608 which intersects the light beam six and two passing through the fluid 605.

As shown in FIG. 7 a filter 714 is placed in front of a sensor 716 to form a front-end portion of spectrometer or 718, which receives light passing through the fluid and optically transmissive member. A force member 709 such as a spring is placed in contact with the optically transmissive member to exert a force on the optically transmissive member. In another embodiment, a different force member can be used, such as a mechanical arm is provided to exert a force on the member. The force presses the optically transmissive member against an adjacent optically transmissive window 604 so that the distance between the optically transmissive member and the optically transmissive window is minimized. Minimizing the distance between the member and the adjacent window reduces reflections between the optically transmissive window and the adjacent optical transmissive window, whenever both windows have the same refractive index because it reduces the thickness of any layer of fluid between the windows that most likely will not have the same refractive index as the windows.

Figure 8:
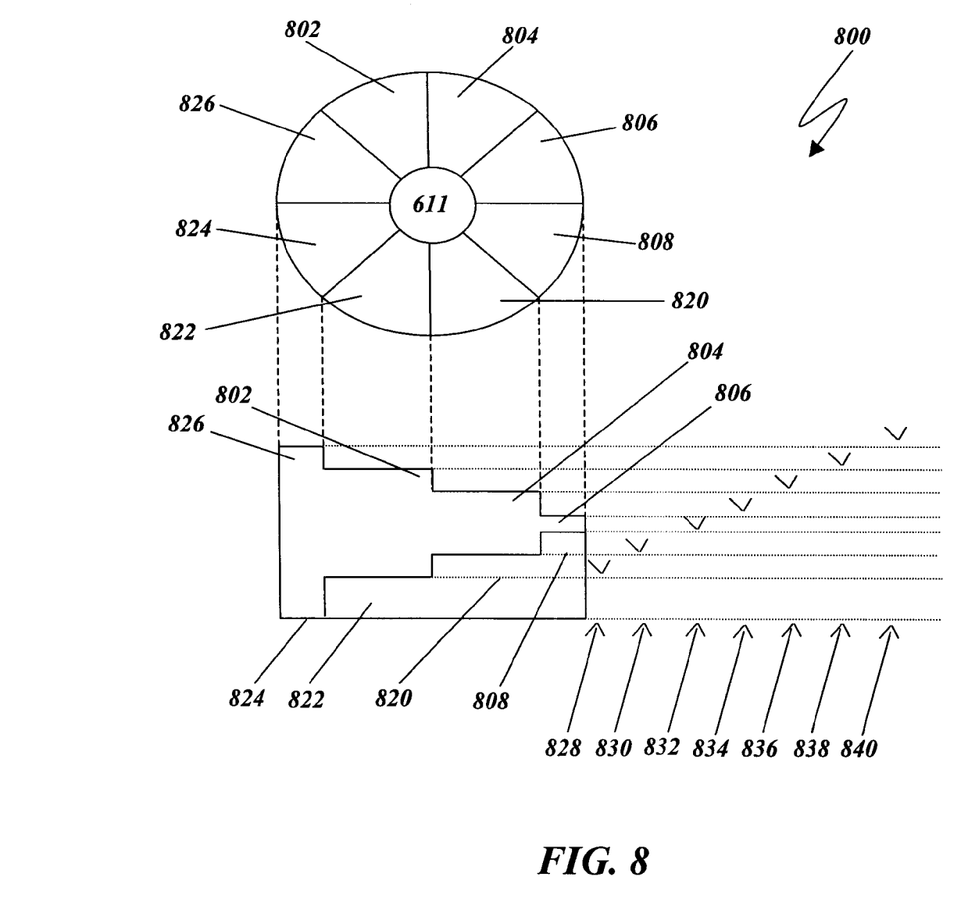
FIG. 8 is a depiction of another illustrative embodiment wherein a round optically transmissive member having sections of varying thickness extending radial from a center axis is provided for insertion into the optical path length.

As shown in FIG. 7D the positioner 610 moves the optically transmissive member down so that a third thicker section is intersecting the light beam and reduces the path length of light passing through the fluid by an amount equal to the thickness of the third section of optically transmissive member. In another illustrative embodiment, the optically transmissive member has a round shape having multiple sections, each of a different thickness. In this embodiment, a positioner rotates the round optically transmissive member around a center axis so that varying thicknesses of the round member intersect the light beam 702 as desired. In another illustrative embodiment, as shown in FIG. 8, optically transmissive member 800 is round and has eight sections 802, 804, 806, 808, 820, 822, 824 and 826. Rotational positioner 611 rotates the varying thickness members to intersect the light beam 602, and vary the length of the optical path through the fluid through which the light travels. As shown in FIG. 8 each section of the member has varying thickness for sections 828, 830, 832, 834, 836, 838 and 840.

Figure 9:
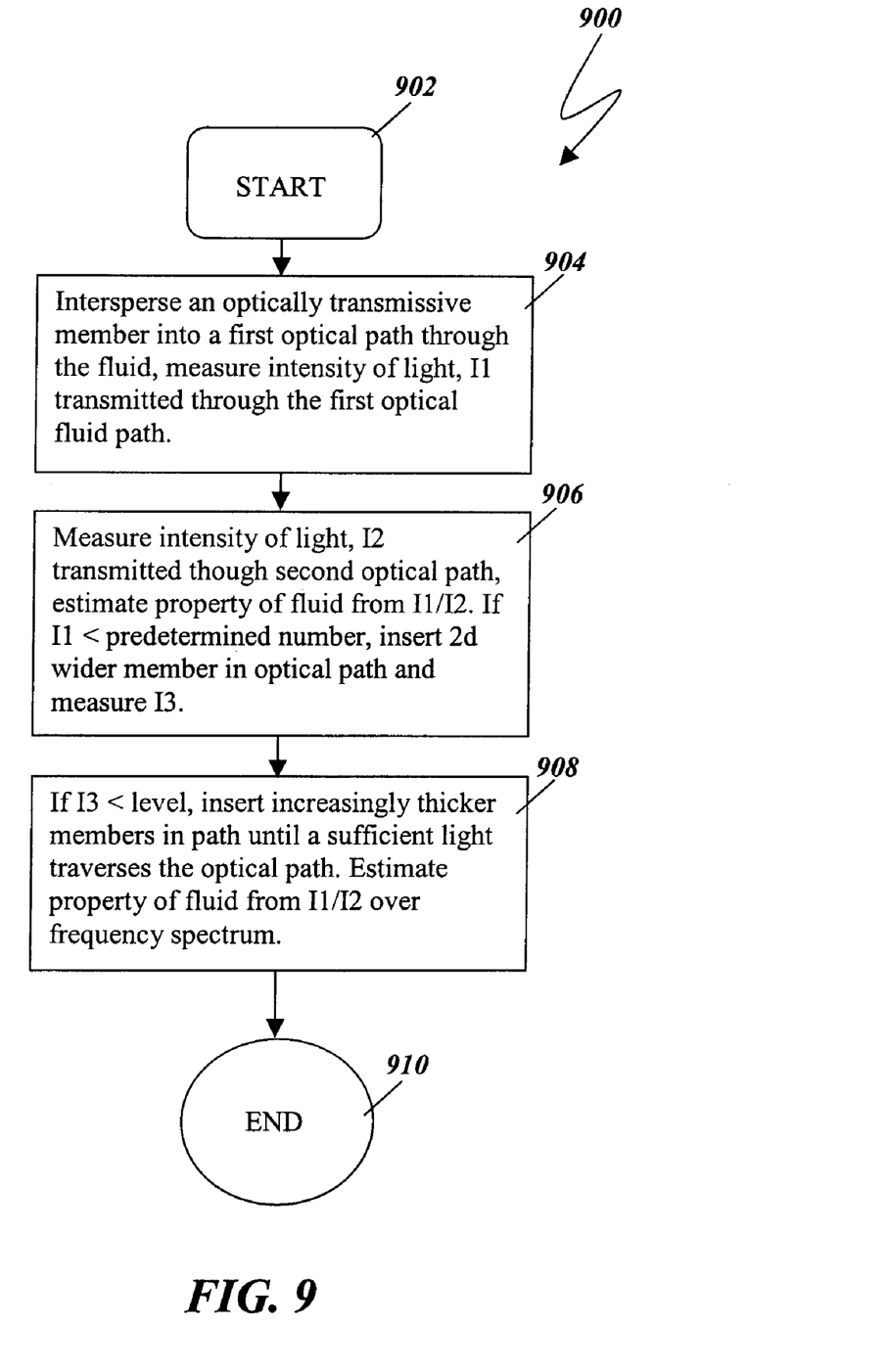
FIG. 9 is a schematic representation of a flowchart showing functions performed in another illustrative embodiment.

Turning now to FIG. 9, a flow chart of functions performed in another illustrative embodiment is illustrated. As shown in FIG. 9 block 902 an illustrative embodiment intersperses an optically transmissive member into a first optical path through the fluid, thereby creating a second shorter optical path through the fluid. At block 904, in another illustrative embodiment, a sensor measures intensity of light, I1 transmitted through the first optical fluid path and measures and intensity of light, I2 transmitted through the second optical path. An estimate of an optical property for the second optical path through the fluid is obtained using a ratio, I1/I2. This estimate of an optical property for the fluid through a the second optical path can be used along with frequency information associated with the amount of light passing through the fluid (OD spectra) to estimate various optical properties for the fluid. These optical properties such as absorbance spectra or light intensity amplitudes over a band of frequencies in the 400-2000 nanometer range as shown in FIG. 5 can be used to estimate various fluid properties based on the optical property or OD spectra.

In another illustrative embodiment, a second optically transmissive member is inserted into the first optical path thereby creating a third optical path shorter than the second optical path. An intensity of light, I2 transmitted through the fluid along the second optical path is measured and intensity of light, I3 transmitted through the fluid along the third optical path is measured. An optical property is estimated for the fluid through the third path from the ratio, I2/I3.

In another illustrative embodiment intensity of light, I1 as shown in block 905 transmitted through the fluid along the first optical path is measured. If I1 is below a predetermined value, the crude oil is too dark for a sufficient amount of light to traverse fluid across the first optical path. Thus an optically transmissive member is inserted or interspersed into the first optical path, thereby creating a second optical path shorter than the first optical path. An intensity of light transmitted through the fluid along the second optical path is measured. As shown in block 908, if the intensity of light traversing the second optical path is insufficient or below a predetermined level assigned for estimating a property of a fluid, increasingly thicker optically transmissive members are inserted in the optical path until a sufficient amount or intensity of light traverses the optical path. A still shorter optical path is then formed and light measured across the still shorter path to estimate an optical property for the fluid.

If the intensity of light is sufficient, the second optical path is used as the reference measurement, an intensity of light I3 transmitted through the fluid along the third optical path is measured. An estimate of an optical property for the fluid through the third path is obtained from the ratio of I2/I3. Successive adjustment of the optical path length when the intensity, I1 measured is below a predetermined value is useful when a particularly dark crude oil is being measured in the fluid passage. For some dark crude oils, an insufficient amount light passes through the initial optical path. Thus, the optical path can be shortened by inserting the optically transmissive member into the path length thereby allowing more light to pass through the dark crude through a shorter optical path.

In another particular embodiment, the optically transmissive member further comprises a plurality of sections, each section having a different thickness. In another particular embodiment, interspersing further comprising interspersed at least two of the plurality of sections into the first optical path to create different optical path lengths through the fluid. In another particular embodiment, the optically transmissive member is round having radial extending steps of varying thickness. In another particular illustrative embodiment, the optically transmissive member has varying thicknesses along a longitudinal axis.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived there from, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

The foregoing example is for purposes of example only and is not intended to limit the scope of the invention which is defined by the following claims.

What is claimed is:

1. A method for changing an optical path length through a fluid downhole, comprising:
   interspersing an optically transmissive member into a first optical path through the fluid, shortening the first optical path, thereby creating a second shorter optical path through the fluid; and
   measuring an intensity of light, $I_1$ transmitted through the first optical path;
   measuring an intensity of light, $I_2$ transmitted through the second optical path; and
   estimating an optical proper for the second optical path from the ratio $I_1/I_2$.

2. The method of claim 1, further comprising:
   estimating a fluid property from the optical property.

3. The method of claim 1, further comprising:
   interspersing a second optically transmissive member into the first optical path, thereby creating a third optical path shorter than the second optical path;
   measuring an intensity of light, $I_2$ transmitted through the fluid along the second optical path;
   measuring an intensity of light, $I_3$ transmitted through the fluid along the third optical path; and
   estimating an optical property for the fluid through the third path from the ratio, $I_2/I_3$.

4. The method of claim 1, further comprising:
   measuring an intensity of light, $I_1$ transmitted through the fluid along the first optical path;
   If $I_1$ is below a predetermined value, interspersing a second optically transmissive member into the first optical path, thereby creating a third optical path shorter than the second optical path;
   measuring an intensity of light, $I_2$ transmitted through the fluid along the second optical path;

measuring an intensity of light, $I_3$ transmitted through the fluid along the third optical path; and estimating an optical property for the fluid through the third path from the ratio, $I_2/I_3$.

5. The method of claim 1, wherein the optically transmissive member further comprises a plurality of sections, each section having a different thickness, the interspersing further comprising interspersing at least two of the plurality of sections into the first optical path to create different optical path lengths through the fluid.

6. The method of claim 5, wherein the optically transmissive member is round, having radial steps of varying thickness.

7. The method of claim 5, wherein the optically transmissive member has steps of varying thickness along a longitudinal axis.

8. The method of claim 1, wherein the fluid is a substantially a gas.

9. The method of claim 1, wherein the first optical path traverses a fluid passage between two optically transmissive windows, the method further comprising:

applying a force to the optically transmissive member to press the optically transmissive member against a surface of an adjacent one of the two optically transmissive windows, thereby substantially reducing reflections of light from an interface between the optically transmissive member and the window surface.

10. The method of claim 9, wherein a distance between the optically transmissive member and the adjacent optically transmissive window is less 3 wavelengths of a frequency of light passing through the optical path.

11. The method of claim 9, wherein the optically transmissive windows and the optically transmissive member have a substantially similar index of refraction.

12. The method of claim 9, wherein the optically transmissive windows and the optically transmissive member are made of sapphire.

13. A system for changing an optical path length through a fluid downhole, comprising:

a fluid passage between two optically transmissive windows for the fluid downhole, the fluid passage having a first optical path through the fluid; and an optically transmissive member for insertion into the first optical path, shortening the first optical path, thereby creating a second shorter optical path through the fluid; and a processor configured to estimate an optical property of the fluid from a ratio of the light measured passing through the first path and the second path.

14. The system of claim 13, further comprising:

a positioner attached to the optically transmissive member that moves the optically transmissive member into the first optical path creating the second optical path.

15. The system of claim 13, wherein the optically transmissive member further comprises a plurality of sections, each section having a different thickness, thereby creating a different path length through the fluid when each section is inserted into the first optical path.

16. The system of claim 13, further comprising:

a force member in contact the optically transmissive member toward an adjacent optically transmissive window, thereby reducing reflection of light from an interface between the optically transmissive member and the adjacent optically transmissive window.

17. The system of claim 13, wherein the optically transmissive window forms a wall of the fluid passage.

18. The system of claim 13, further comprising:

a light sensor for measuring light passing through the fluid along the first optical path and the second optical path.

19. The system of claim 13, further comprising:

a light source positioned adjacent an optically transmissive window; and a filter positioned between the light source and a light sensor, the filter selectively passing frequencies of light from the light source to the light sensor along the first and second optical paths through the fluid.

20. The system of claim 13, wherein the optically transmissive member and the optically transmissive windows have substantially the same index of refraction.

21. The system of claim 13, wherein the optically transmissive member and the optically transmissive windows are made of sapphire.

22. The system of claim 13, wherein the fluid is a gas.

23. The system of claim 13, wherein a shape for the optically transmissive member is selected from the group consisting of round having radial steps of varying thickness and steps of varying thickness along a longitudinal axis.

24. A downhole tool for estimating a property of a fluid, comprising:

a tool housing suitable for traversing a borehole, adjacent an earth borne fluid formation;

a port in the tool housing for entry of fluid from the formation;

a fluid passage in fluid communication with the port, the fluid passage having a first optical path through the fluid;

an optically transmissive member movably mounted for insertion into the first optical path length, shortening the first optical path, creating a second shorter optical path through the fluid;

a positioner attached to the optically transmissive member that inserts the optically transmissive member into the optical path;

a light sensor for measuring light passing through the fluid along the first path and the second path;

a filter positioned between the light sensor and the light source for selectively passing frequencies of the light from the light source to the light sensor along the first and second optical path; and a processor for estimating an optical property of the fluid from a ratio of the light measured passing through the fluid along the first path to the light measured passing through the second path.

* * * * *